United States Patent
Bigus et al.

(12) 
(10) Patent No.: US 6,527,739 B1
(45) Date of Patent: Mar. 4, 2003

(54) SPIRALED BALLOON ARRANGEMENT FOR TREATMENT OF A TORTUOUS VESSEL

(75) Inventors: Steve Bigus, San Jose; Carl Simpson, Los Altos; Kevin M. Mauch, Windsor, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/752,203

(22) Filed: Dec. 29, 2000

(51) Int. Cl.[7] ............................................... A61M 29/00
(52) U.S. Cl. ................................................. 604/101.01
(58) Field of Search ................................. 606/191, 192, 606/194; 604/101.01, 101.03, 101.05, 101.04, 96.01, 99.01

(56) References Cited

U.S. PATENT DOCUMENTS

| | | |
|---|---|---|
| 4,581,017 A | 4/1986 | Sahot |
| 4,983,167 A | 1/1991 | Sahota |
| 5,019,042 A | 5/1991 | Sahota |
| 5,176,619 A | 1/1993 | Segalowitz |
| 5,226,889 A | 7/1993 | Sheiban |
| 5,295,960 A | 3/1994 | Aliahmad et al. |
| 5,308,356 A * | 5/1994 | Blackshear, Jr. et al. ... 606/194 |
| 5,383,856 A * | 1/1995 | Bersin ................... 604/101.01 |
| 5,395,333 A | 3/1995 | Brill |
| 5,415,637 A | 5/1995 | Khosravi |
| 5,545,132 A | 8/1996 | Fagan et al. |
| 5,618,266 A | 4/1997 | Liprie |
| 5,643,171 A | 7/1997 | Bradshaw et al. |
| 5,716,340 A | 2/1998 | Schweich, Jr. et al. |
| 5,725,535 A | 3/1998 | Hegde et al. |
| 5,782,740 A | 7/1998 | Schneiderman |
| 5,782,855 A | 7/1998 | Lau et al. |
| 5,868,777 A | 2/1999 | Lam |
| 5,908,448 A | 6/1999 | Roberts et al. |
| 5,910,101 A | 6/1999 | Andrews et al. |
| 5,938,582 A | 8/1999 | Ciamacco, Jr. et al. |
| 5,947,924 A | 9/1999 | Liprie |
| 5,976,106 A | 11/1999 | Verin et al. |
| 6,013,054 A | 1/2000 | Jiun Yan |
| 6,022,359 A | 2/2000 | Frantzen |
| 6,048,350 A | 4/2000 | Vrba |
| 6,117,064 A | 9/2000 | Apple et al. |

FOREIGN PATENT DOCUMENTS

| | | |
|---|---|---|
| EP | 0 688 580 A1 | 12/1995 |
| WO | WO 97/40889 | 11/1997 |
| WO | WO 98/01183 | 1/1998 |

OTHER PUBLICATIONS

U. S. Patent Application Ser. No. 09/024,327, Andrews et al.
U. S. Patent Application Ser. No. 09/448,654, Andrews et al.
U.S. Patent Application Ser. No. 09/024,079, Chiu et al.

* cited by examiner

*Primary Examiner*—Kevin T. Truong
(74) *Attorney, Agent, or Firm*—Blakely, Sokoloff, Taylor & Zafman LLP

(57) ABSTRACT

A catheter balloon arrangement for application in tortuous blood vessels. First and second spiraled balloons are coupled to a catheter body portion. The spiraled balloons can have first and second apexes with a pitch length there between configured to encourage tortuous compatibility between the catheter balloon arrangement and a body lumen. A method of treatment with an embodiment of a catheter balloon arrangement is also provided.

25 Claims, 6 Drawing Sheets

SPIRALED BALLOON ARRANGEMENT FOR TREATMENT OF A TORTUOUS VESSEL

BACKGROUND OF THE INVENTION

The present invention relates generally to the application of catheters for angioplasty procedures. More particularly, the present invention relates to a balloon catheter for treating diffuse disease localized in tortuous blood vessels.

BACKGROUND OF THE PRIOR ART

In a typical coronary catheter procedure, a balloon catheter is first introduced into the cardiovascular system of a patient through the brachial or femoral artery and is advanced therein until a balloon of the catheter is disposed adjacent a treatment site of the coronary artery to be treated. The catheter is twisted and torqued from its proximal end, nearest the user, to turn its distal tip so that it can be guided to the treatment site. By way of example a percutaneous transluminal coronary angioplasty (PTCA) catheter procedure is considered. The treatment site may contain a diseased portion partially occluded by an atheroma. In the case of a PTCA catheter procedure, the balloon is positioned across the atheroma. Once in position, the balloon of the catheter is inflated to a predetermined size to radially dilate the vessel and compress the atheroma. This increases effective diameter of the previously occluded blood vessel. The balloon is then deflated so that the catheter can be removed and blood flow resumed through the dilated artery or blood vessel.

Other catheter procedures make use of catheter balloons. In addition to the dilation catheter, catheters are used in radiotherapy, drug delivery, stent placement and other procedures, including non-coronary procedures.

Conventional catheter balloons possess several disadvantages. For example, most dilation, radiotherapy, drug-delivery, and stent placement catheters utilize a single balloon that is continuous, tube-shaped, and usually greater than ten millimeters in length. Upon inflation in a vessel region or treatment site that is naturally curved, the long shape of the balloon places an uneven distribution of expansive stress throughout the vessel and can cause the vessel to straighten. The stress applied to the vessel walls in this manner can result in vessel trauma and procedural complications. Such trauma can include damage to endothelial cells during insertion, inflation, and withdrawal of the balloon and catheter. This damage can encourage the formation of atheromas discouraging the purpose of the procedure and impeding blood flow. Therefore, what is needed is a catheter balloon arrangement for treatment of a tortuous vessel.

SUMMARY OF THE INVENTION

In an embodiment of the invention a catheter balloon arrangement includes an elongated catheter body portion. First and second spiraled balloons are provided about the elongated catheter body portion.

In another embodiment a catheter balloon arrangement includes a catheter body portion. First and second spiraled balloons with first and second apexes are coupled to the catheter body portion. A pitch length between the apexes encourages tortuous compatibility between the catheter balloon arrangement and a tortuous body lumen.

A method of the invention includes advancing an embodiment of a catheter balloon arrangement through a body lumen in a deflated state. The catheter balloon arrangement is inflated and treatment provided to the body lumen.

BRIEF DESCRIPTION OF THE DRAWINGS

The present invention is illustrated by way of example, and not limitation, in the figures of the accompanying drawings in which.

DETAILED DESCRIPTION OF THE INVENTION

The present invention provides many advantages for treating a body lumen, including treatment of a tortuous vessel by dilation, radiotherapy, drug delivery, stent placement and other procedures. While the invention is described in detail as applied to coronary artery treatments, those skilled in the art will appreciate that the present invention can also be used in treatment of other body lumen, such as peripheral arteries and veins.

In a method for treating a diseased portion of a tortuous coronary artery, a guidewire is first inserted through the brachial or femoral artery to a position past the treatment area. In embodiments of the present invention a catheter assembly is equipped with a balloon arrangement. The catheter is advanced to the diseased portion of the tortuous coronary artery by following the guidewire through a guidewire lumen of the catheter. The balloon arrangement remains deflated during this advancement.

Once positioned, a syringe or an inflation/deflation device, commonly referred to as an indeflator, introduces an inflation medium through one or more inflation lumen to the balloon arrangement. The inflation medium fills the inflation lumen and inflates the balloon arrangement. The inflation medium is preferably a contrast medium. However, in alternate embodiments, compressed air, nitrogen, argon, saline, and helium are used.

Figure 1:
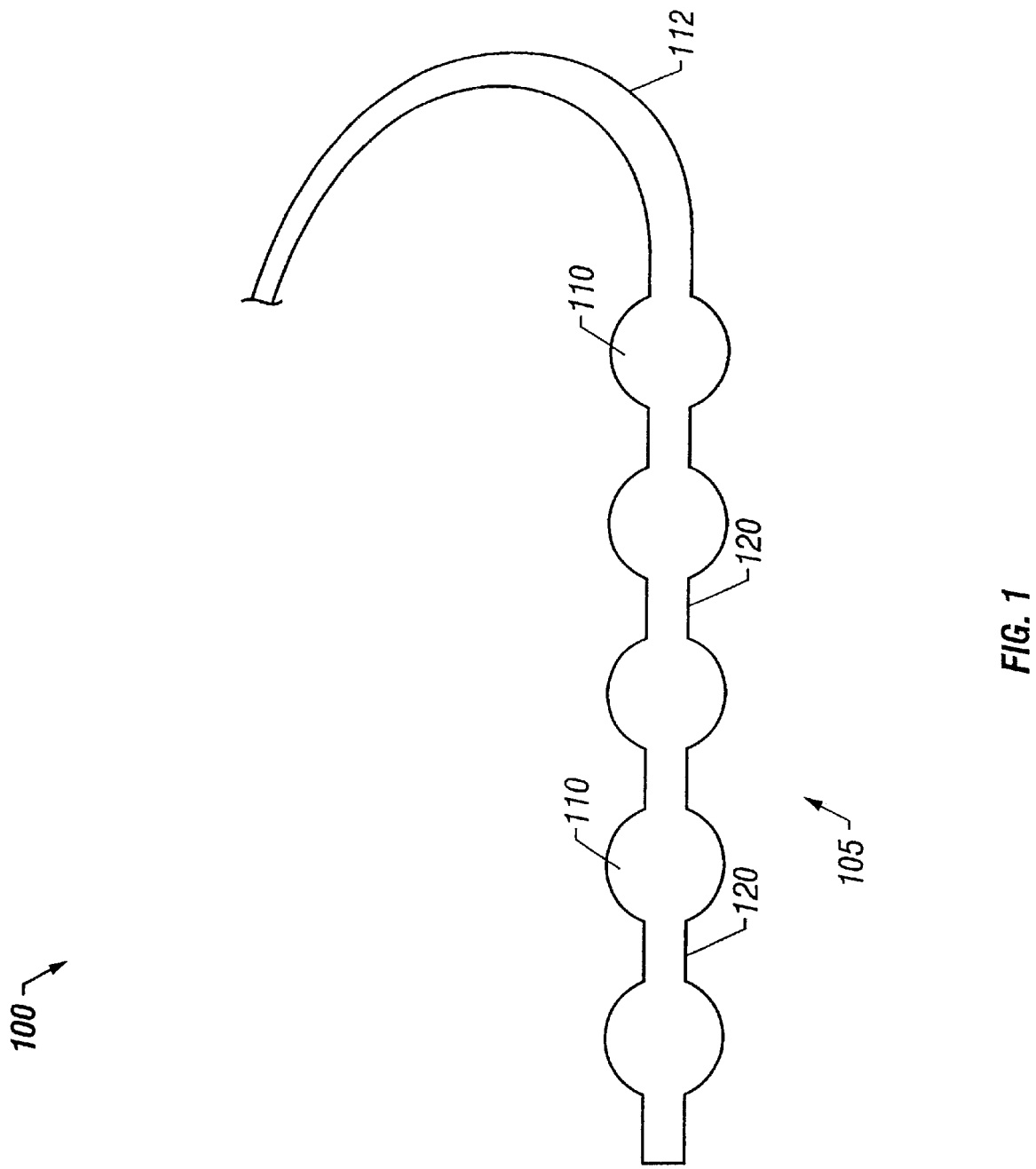
FIG. 1 is a pictorial view of an embodiment of the invention
Figure 2:
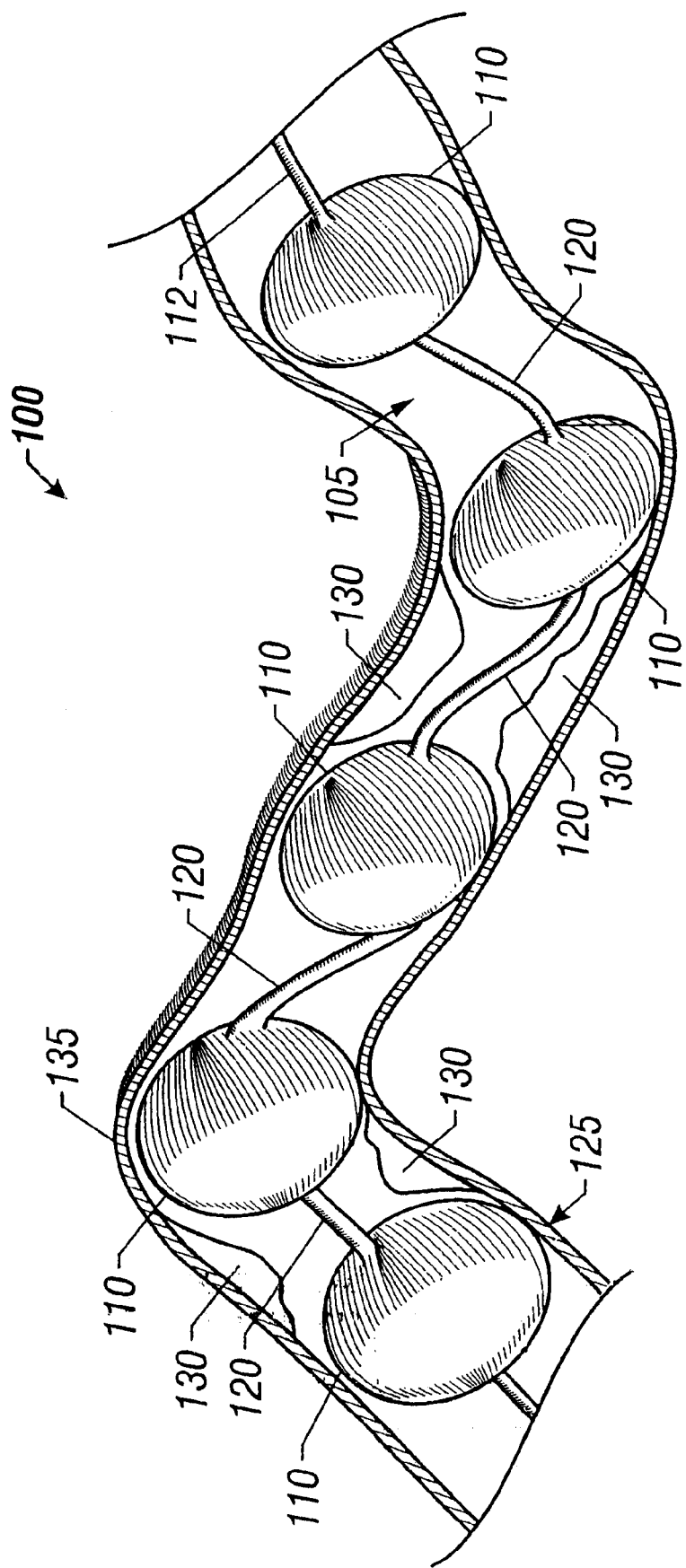
FIG. 2 is a side view of a portion of the embodiment of FIG. 1 shown within a cross-section of a tortuous vessel.

Referring to FIG. 1 an embodiment of a catheter assembly 100 of the present invention is shown. FIG. 2 shows the catheter assembly 100 within a tortuous blood vessel 125. The segmented balloon arrangement 105 is at the distal end of the catheter assembly 100. The catheter assembly 100 includes a segmented balloon arrangement 105. The segmented balloon arrangement 105 has balloon segments 110 organized in a series near the distal end of the catheter assembly 100.

The balloon segments 110 are joined by connector segments 120. Connector segments 120 join adjacent balloon segments 110 in continuous contact. Connector segments 120 have flexible properties to bend with a catheter body 112. A diameter of a connector segment 120 is comparable to a diameter of the catheter body 112. Flexible connector segments 120 also exhibit non-inflatable properties, such that when balloon segments 110 inflate, connector segments 120 maintain a substantially constant radial diameter, while conforming to the curves of a tortuous blood vessel 125.

The catheter assembly 100 includes any number of balloon segments 110. In the deflated state, the diameters of the balloon segments 110 are generally comparable to the diameter of the catheter body 112. Upon inflation, the configuration of the balloon segments 110 promotes conformability to the tortuous blood vessel 125. Additionally, each balloon segment 110 may be inflated to a unique size and shape as compared to other balloon segments 110 of the segmented balloon arrangement 105. In an embodiment of the invention, as explained further herein, this unique size and shape is accomplished by use of separate inflation lumen for separate balloon segments 110. However, in an alternate embodiment, the balloon segments 110 share a common inflation lumen but nevertheless are inflatable to an independently predetermined size and shape.

Typically, each balloon segment 110 is from about 5 to about 25 millimeters in length. Shorter balloon segment 110 lengths discourage straightening of the tortuous blood vessel 125 upon inflation of the segmented balloon arrangement 105. However, other embodiments can utilize segments of other lengths.

In an embodiment of the invention the length of connector segments 120 between adjacent balloon segments 110 varies. For example, the distance between one pair of adjacent balloon segments 110 is as short as 5 millimeters, whereas the distance between another pair of adjacent balloon segments 110 is as long as 25 millimeters. Varying these lengths allows for a unique segmented balloon arrangement 105 useful for treatment of such a uniquely shaped tortuous blood vessel 125.

In an embodiment of the invention connector segment 120 length is varied where diseased areas are localized at unevenly spaced apart portions of the tortuous blood vessel 125. In this way a single treatment is effectively applied to all diseased areas simultaneously.

The overall segmented balloon arrangement 105 is of any length, and typically will range between about 10 and about 50 millimeters. The specific characteristics of each segmented balloon arrangement is customized to the patient's needs as determined by his or her physician.

The balloon segments 110 of the embodiment shown are formed by a single molding process producing an arrangement of alternating balloon segments 110 and connector segments 120. The wall thickness of the connector segments 120 is increased during the molding process. Thicker walls of the connector segments 120 resist inflation.

In an alternate embodiment connector segments 120 are made of inherently non-inflatable material, while inflatable material is used for balloon segments 110. The individual balloon segments 110 are blown individually and attached to a body of the catheter in a spaced apart manner. Thus, providing a space between the balloon segments 110 when placed about the body of the catheter provides the connector segments 120.

FIG. 2 shows the tortuous blood vessel 125 having several diseased areas 130. Portions of the tortuous blood vessel 125 in FIG. 2 are further labeled to designate peaks 135 and valleys 140 of the tortuous blood vessel 125 that constitute bends or curves. The segmented balloon arrangement 105 is deployed within the tortuous blood vessel 125. Segmented balloon arrangement 105, when disposed and inflated within tortuous blood vessel 125, allows the catheter assembly 100 to flex and to conform to the tortuous blood vessel 125. This flexibility allows balloon segments 105 to bend transversely along a vessel axis through the center of tortuous blood vessel 125. As a result, the tortuous blood vessel 125 retains its pre-catheterized shape without added trauma even though balloon segments 120 have been inflated.

Figure 3:
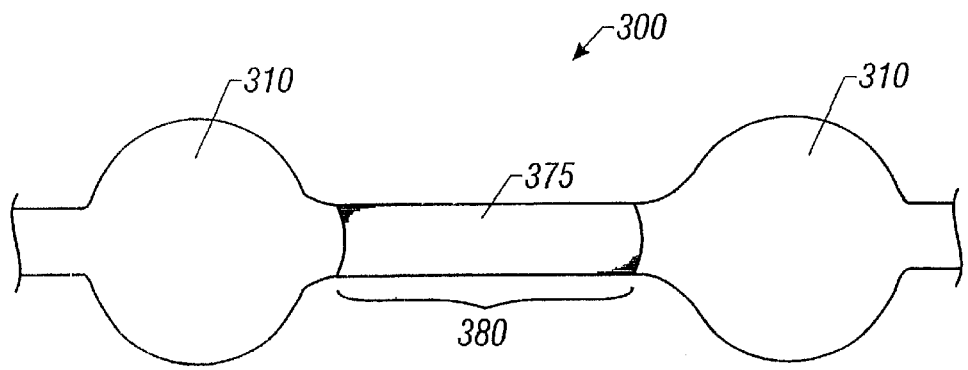
FIG. 3 is a side view of an embodiment of the invention.

FIG. 3 shows an alternate embodiment of a segmented balloon arrangement 300. The balloon segments 310 are formed by clamping a restriction ring 375 of a desired diameter about a portion of an inflatable balloon (not shown). The balloon segments 310 arise from that portion of the inflatable balloon which is not clamped by the restriction ring 375.

The restriction ring 375 does not block inflation and guidewire lumens (not shown) running through the center of the balloon arrangement 300. The restriction ring 375 remains relatively fixed in diameter, but nevertheless remains flexible upon inflation of the balloon segments 310. The restriction ring 375 is formed from materials such as flexible sheaths or polymeric bands. In one embodiment the restriction ring 375 includes radiopaque materials to improve the visibility of the balloon arrangement 300. For example, a metallic band can be incorporated into the restriction ring 375. For practical purposes, the balloon arrangement 300 will generally have more than one restriction ring 375 to form many balloon segments 310.

In one embodiment a restriction ring 375 is clamped during the manufacturing process before the catheter assembly is delivered to the customer. Thus, this embodiment provides for customized balloon segment 310 spacing for treatment.

Figure 4:
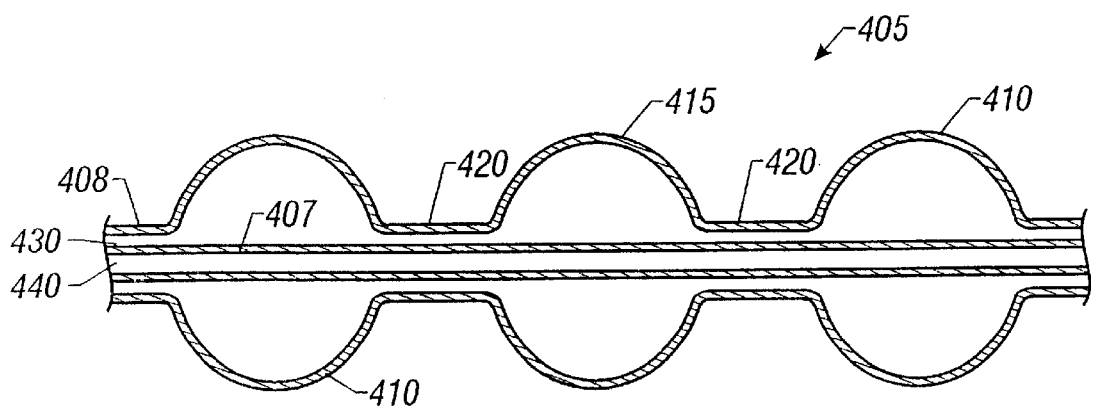
FIG. 4 is a cross-sectional view of an embodiment of the invention.

FIG. 4 show a cross sectional view of an embodiment of a balloon arrangement 405 in an inflated state. A guidewire lumen 440 extends along the center of the balloon arrangement 405 through a shaft 407. Segmented balloons 410, 415 share common inflation lumen 410 formed by the space between the shaft 407 and a sheath 108 surrounding the shaft 407. A single inflation lumen 430 is used in inflating all segmented balloons 410, 415 shown. However, as shown, middle segmented balloon 415 is smaller than outer segmented balloons 410. This is because the balloon segments 410, 415 are inflatable to predetermined sizes and shapes.

Figure 5:
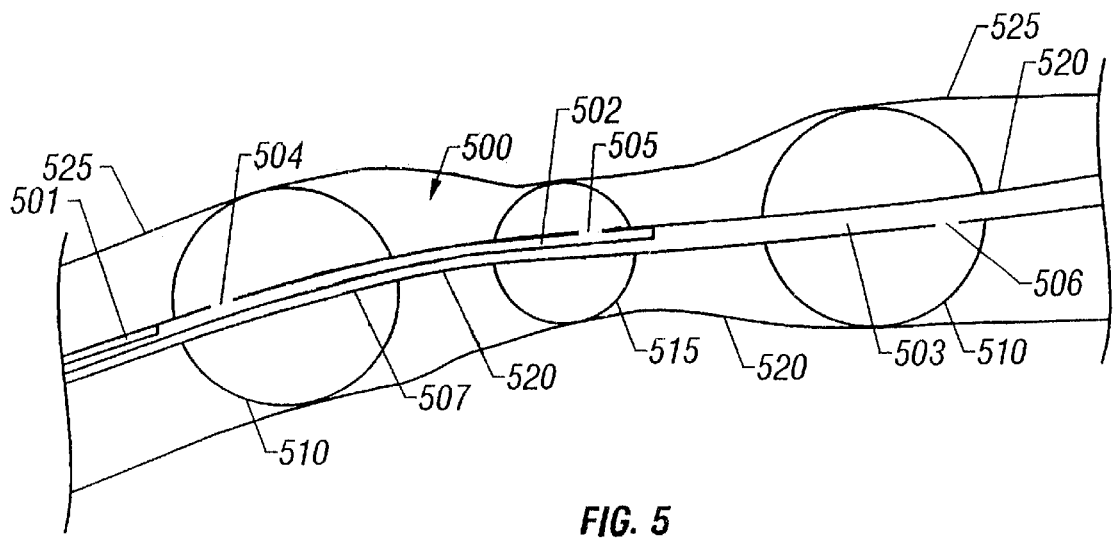
FIG. 5 is a cross-sectional view of an embodiment of the invention shown within a cross-section of a tortuous vessel.

Referring to FIG. 5, in an alternate embodiment of a balloon arrangement 500 is shown. Namely, multiple inflation lumen 501, 502, 503 are provided through shaft 507. That is, each balloon segment 510, 515 is provided with its own independent inflation lumen 501, 502, 503. Thus, each balloon segment 510, 515 is inflatable to a distinct pressure and even with a distinct media, if desired. As shown, outer balloon segments 510 are inflatable by way of outer inflation lumen 501, 503 via outer balloon ports 504, 506. The middle balloon segment 515 is inflatable by way of a middle inflation lumen 502 via a middle balloon port 505. In an alternate embodiment outer balloon segments 515 may share a common inflation lumen (not shown) independent of the middle balloon lumen 502.

FIG. 5 shows how such a degree of inflation selectivity can be utilized. The balloon arrangement 500 is shown within a tortuous vessel 525. The tortuous vessel 525 has a narrow vessel portion 520. As a result, in a method of the invention, the middle balloon segment 515 is inflated to a level comparable to the size of a narrow vessel portion 520 when adjacent thereto. Similarly, in another method of the invention, the balloon arrangement 405 embodiment of FIG. 4 accounts for a possible narrow vessel portion adjacent the segmented balloon 415 in a predetermined manner.

Additionally, in another method of the invention, selectively inflating balloon segments 510, 515 with independent inflation lumen 501, 502, 503 is used to control the flexibility of the balloon arrangement 500. In this method the middle balloon segment 515 is inflated first, then the outer balloon segments 510 are inflated to better conform the balloon arrangement 500 to the tortuous blood vessel 525. In one embodiment, the middle balloon segment 515, when fully inflated, is not as large as the outer balloon segments 510. This allows the balloon arrangement 500 to have a greater stretch of curvature between the outer balloon segments 510.

In another method of the invention, the segmented balloon arrangement 500 is used for site-specific drug delivery. The outer balloon segments 510 are used to seal off the region of the blood vessel there between, allowing for prolonged site-specific drug delivery between the outer balloon segments 510. Meanwhile the middle balloon lumen 502 is used to deliver a drug to the narrow vessel portion 520 through the middle balloon segment 515, such as where the middle balloon segment 515 is a micro-porous balloon. That is, in one embodiment the middle balloon segment 515 is made of a porous membrane to allow drug delivery to the surrounding tortuous blood vessel 525.

Figure 6:
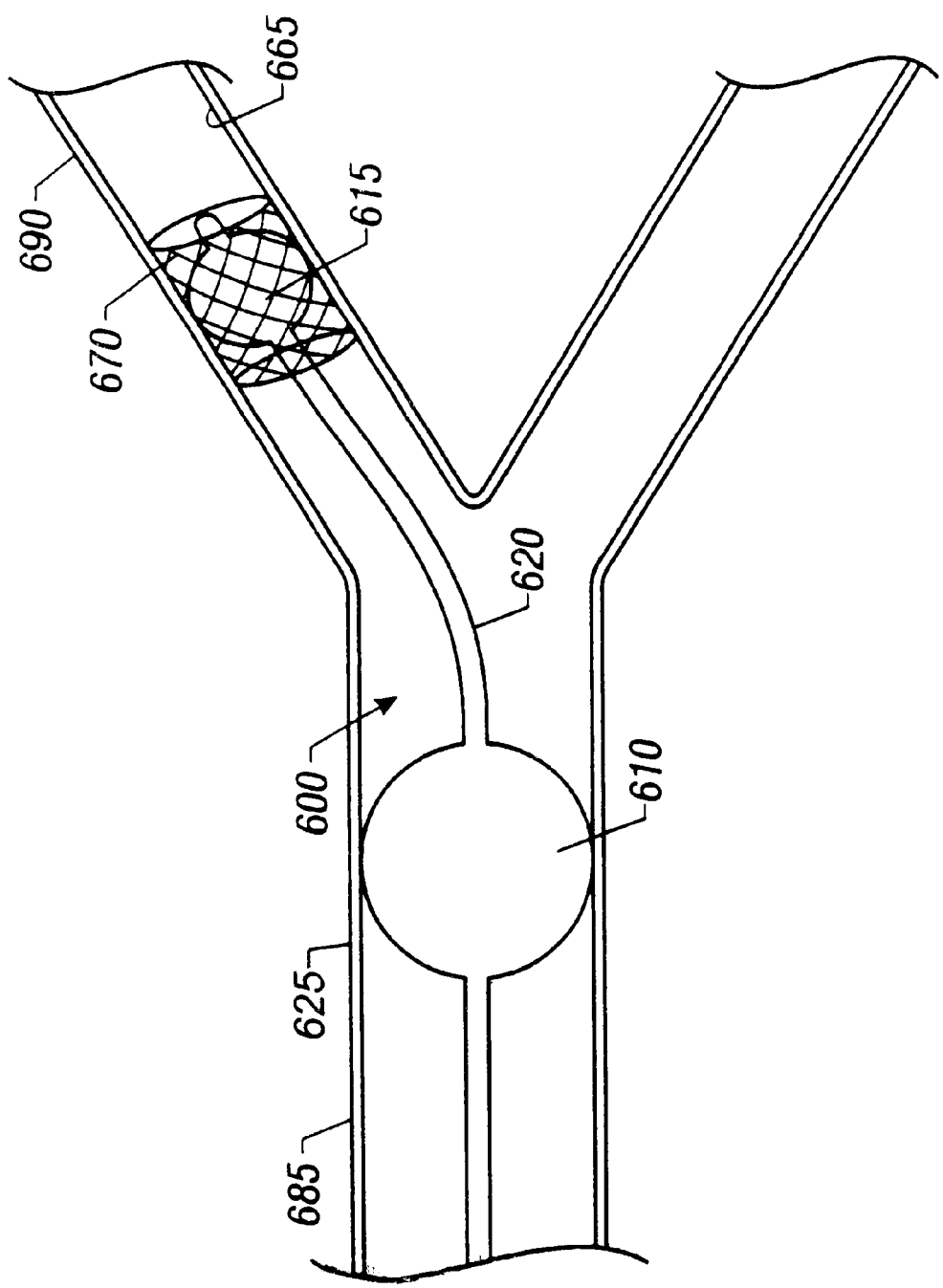
FIG. 6 is a side view of an embodiment of the invention shown within a cross-section of a tortuous vessel.

FIG. 6 shows an embodiment of a balloon arrangement 600 positioned within a tortuous vessel 625 which is a bifurcated vessel. As shown, a diseased area is located in a narrow branch 690 portion of a tortuous vessel 625, making the diseased area difficult to treat with conventional balloon catheters. A proximal balloon segment 610 and a distal balloon segment 615 are coupled by a flexible connector segment 620. The proximal balloon segment 610 is positioned within a parent blood vessel 685 of the tortuous vessel 625. Alternatively, the distal balloon segment 615 is positioned within the separate narrow branch 690 of the tortuous vessel 625. The distal balloon segment 615 has a smaller radial diameter compared to the proximal balloon segment 610. As a result, a treatment, such as stent placement (as shown) can account for the narrower size of the narrow branch 690 as compared to the parent blood vessel 685. The differing sizes of the balloon segments 610, 615 are accounted for by independent inflation lumen or independently predetermined balloon segment sizes as discussed previously.

FIG. 6 illustrates a method of stent placement within the narrow branch 690. While the proximal balloon segment 610 stabilizes the catheter, the distal balloon segment 615 is inflated via an independent inflation lumen, to deploy a stent 670 at a vessel wall 665. In an alternate method, stabilization and stent deployment occur simultaneously where the balloon segments 610, 615 share a common lumen.

Figure 7:
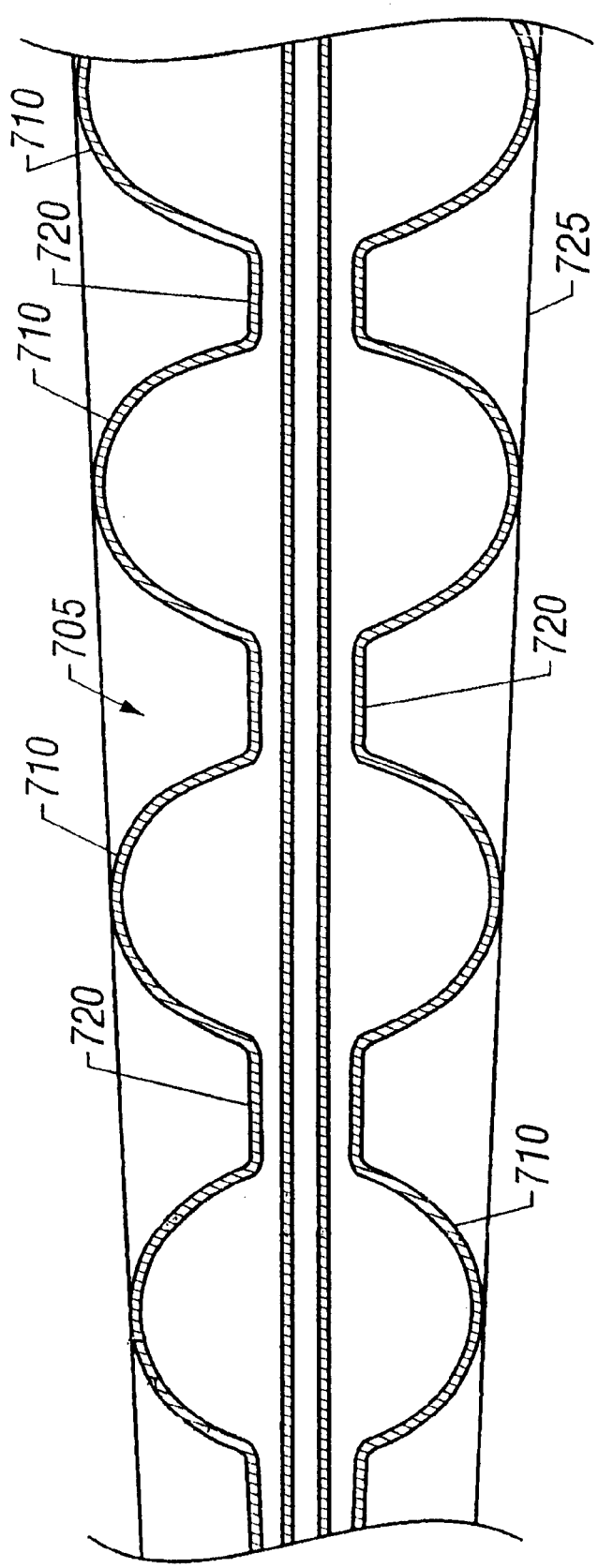
FIG. 7 is a cross-sectional view of an embodiment of the invention shown within a cross-section of a tortuous vessel.

FIG. 7 shows an alternate embodiment of a balloon arrangement 705 for treatment of a tortuous blood vessel 725 that is tapered. The balloon arrangement 705 is shown having increasing diameters for balloon segments 710 in regions of the tortuous blood vessel 725 that increase in size. As shown, the proximal balloon segment 710 has the smallest inflated diameter, and each subsequent balloon segment 710 distally increases in diameter. This segmented balloon arrangement 705 conforms generally to the increase in the tortuous blood 725 vessel size that is common when a catheter is inserted within a blood vessel distant from the heart and is then advanced toward the heart. In one embodiment of the invention, the size difference between balloon segments 710 is predetermined. In an alternate embodiment of the invention, the size difference between balloon segments 710 is provided by separate and independent inflation lumen for each separate balloon segment 710.

In an alternate embodiment, segmented balloons of decreasing diameters (not shown), from the proximal to the distal end, are used when treating blood vessels that narrow in diameter (i.e. moving away from the heart). In another embodiment, a segmented balloon arrangement is provided in which a cluster of balloon segments with comparatively large diameters is followed by a cluster with comparatively smaller diameters. Again, the size difference between the distinguishable clusters of balloon segments is provided by an independently predetermined balloon segment size or independent inflation lumen for each balloon segment cluster.

Figure 8:
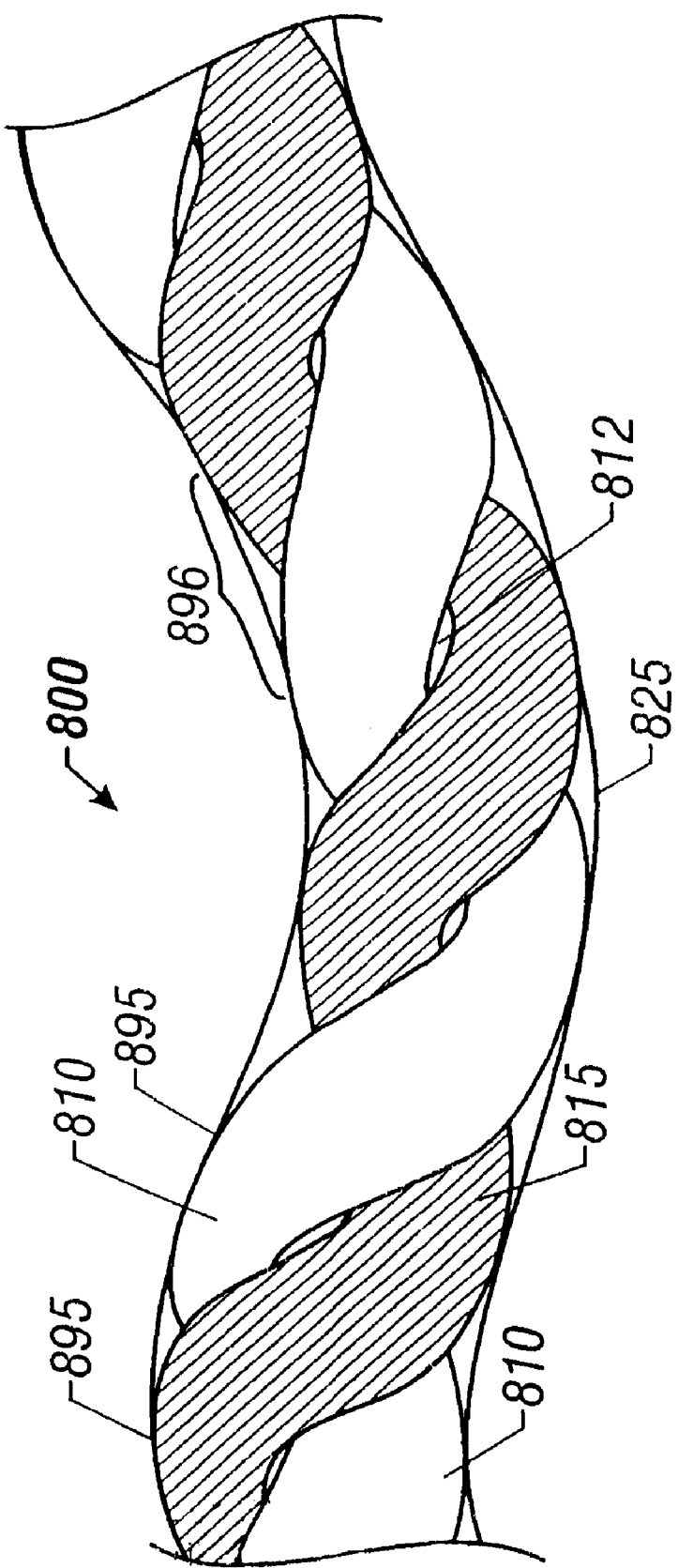
FIG. 8 is a side view of an embodiment of the invention shown within a cross-section of a tortuous vessel.

FIG. 8 illustrates another embodiment of a balloon arrangement 800. The balloon arrangement 800 has balloon segments in the form of first 810 and second 815 balloons coiled around catheter body 812. First and second balloons 810, 815 are coiled in a helical conformation attached near the distal end of catheter body 812. In an alternate embodiment more than two helical balloons (not shown) are provided.

At periodic areas, the outer surfaces of first and second balloons 810, 815 are adhered to the catheter body 812. In an alternate embodiment, first and second balloons 810, 815 are adhered to the catheter body 812 continuously. The catheter body 812 has flexible properties, allowing the first and second balloons 810, 815 to conform to a tortuous blood vessel 825. The balloon arrangement 800 is configured to allow perfusion of blood between the first and second balloons 810, 815 through tortuous blood vessel 825.

The balloon arrangement 800 shown is again configured to conform to the shape of a tortuous blood vessel 825 without causing added injury thereto upon inflation. The balloon arrangement 800 has definable pitch lengths 896. The pitch length 896 is the distance from one apex 895 of first balloon 810 to an adjacent apex 895 of second balloon 815. The pitch length 896 can be varied in the manner by which first and second balloons 810, 815 are attached to catheter body 812.

Shorter pitch lengths 896 provide added flexibility to the balloon arrangement 800. Therefore, in an embodiment of the invention a balloon arrangement 800 is provided wherein pitch lengths 896 are intentionally varied based on the particular tortuous vessel 825 configuration given. For example, pitch lengths 896 of comparatively shorter lengths are provided in areas where the balloon arrangement 800 is to be adjacent comparatively sharper curves of tortuous vessel 825 while pitch lengths 896 of comparatively larger lengths are provided in areas where the balloon arrangement 800 is to be adjacent comparatively straighter portions of tortuous vessel 825. In this manner a customized balloon arrangement 800 is provided.

In an embodiment of the invention separate inflation lumen are used to inflate the individual balloons 810, 815. In a method of using these separate inflation lumen the first balloon 810 is inflated to a larger size than the second balloon 815 in order to enhance perfusion of blood across the balloon arrangement 800 within the tortuous blood vessel 825. In fact, in one embodiment, the second balloon 815 is not inflated at all. Alternatively, in another embodiment of the invention, the individual balloons 810, 815 are of different predetermined sizes and share a common lumen. Nevertheless perfusion is enhanced as one of the balloons 810 or 815 is of a smaller size avoiding contact with the tortuous blood vessel 825 and thus, enhancing perfusion there across.

Embodiments of the invention include balloon arrangements that can avoid the tendency to straighten or otherwise injure a tortuous vessel during a catheter procedure. These embodiments include advantages associated with the use of independently predetermined balloon segment sizes, balloon segments having independent inflation lumen, and balloon segments promoting perfusion through a body lumen during treatment thereof.

Although exemplary embodiments of the invention have been shown and described modifications can be made to the present invention without departing from the spirit and scope thereof. The specific dimensions and materials of construction are provided as examples and substitutes are readily contemplated which do not depart from the invention.

What is claimed is:

1. An apparatus comprising:
    an elongated catheter body portion;
    a first spiraled balloon about said elongated catheter body portion; and
    a second spiraled balloon about said elongated catheter body portion, wherein said first and second spiraled balloons have separate inflation sources.

2. The apparatus of claim 1 wherein said first spiraled balloon runs parallel said second spiraled balloon about said elongated catheter body portion.

3. The apparatus of claim 1 further comprising:
    a first apex of said first spiraled balloon;
    a second apex of said second spiraled balloon; and
    a pitch length between said first apex and said second apex, said pitch length to encourage tortuous compatibility between said apparatus and a tortuous body lumen at said pitch length when said apparatus is inflated within said tortuous body lumen.

4. The apparatus of claim 1 wherein said first spiraled balloon is inflatable to a first size and said second spiraled balloon is inflatable to a second size when said first balloon is inflated to said first size, said first size different than said second size to enhance perfusion of a body fluid past said apparatus when inflated within a body lumen.

5. The catheter balloon arrangement of claim 4 wherein said first size and said second size are predetermined sizes.

6. The apparatus of claim 4 further comprising:
    a first inflation lumen coupled to said first spiraled balloon; and
    a second inflation lumen coupled to said second spiraled balloon.

7. A catheter balloon arrangement comprising:
    a catheter body portion;
    a first spiraled balloon coupled to said catheter body portion and having a first apex;
    a second spiraled balloon coupled to said catheter body portion and having a second apex; and
    a variable pitch length between said first apex and said second apex, said pitch length to encourage tortuous compatibility between said catheter balloon arrangement and a tortuous body lumen when said catheter balloon arrangement is inflated within said tortuous body lumen.

8. The catheter balloon arrangement of claim 7 wherein said first spiraled balloon is inflatable to a first size and said second spiraled balloon is inflatable to a second size when said first balloon is inflated to said first size, said first size different than said second size to enhance perfusion of a body fluid past said catheter balloon arrangement when inflated within a body lumen.

9. The catheter balloon arrangement of claim 8 wherein said first size and said second size are predetermined sizes.

10. The catheter balloon arrangement of claim 8 further comprising:
    a first inflation lumen coupled to said first spiraled balloon; and
    a second inflation lumen coupled to said second spiraled balloon.

11. A method comprising:
    advancing a deflated catheter balloon arrangement through a body lumen to a treatment site, said catheter balloon arrangement including a first spiraled balloon and a second spiraled balloon about an elongated catheter body portion, said first and second spiraled balloons having separate inflation sources;
    inflating said catheter balloon arrangement; and
    treating said body lumen at said treatment site.

12. The method of claim 11 wherein said treating further comprises delivering radiotherapy to said treatment site via said catheter balloon arrangement.

13. The method of claim 11 wherein said body lumen is a tortuous body lumen, said first spiraled balloon includes a first apex, said second spiraled balloon includes a inflation medium via a second inflation to achieve a second size, said first size different from said second size to enhance said perfusing.

14. The method of claim 11 further comprising perfusing a body fluid past said catheter balloon arrangement during said treating.

15. The method of claim 14 wherein said inflating further comprises:
    filling said first spiraled balloon with a first inflation medium via a first inflation lumen to achieve a first size of said first spiraled balloon; and
    filling said second spiraled balloon with a second inflation medium via a second inflation to achieve a second size, said first size different from said second size to enhance said perfusing.

16. A catheter balloon arrangement comprising:
    a catheter body portion;
    a first spiraled balloon coupled to said catheter body portion and having a first apex;
    a second spiraled balloon coupled to said catheter body portion and having a second apex, said first and second spiraled balloons having separate inflation sources; and
    a variable pitch length between said first apex and said second apex, said pitch length to encourage tortuous compatibility between said catheter balloon arrangement and a tortuous body lumen when said catheter balloon arrangement is inflated within said tortuous body lumen.

17. An apparatus comprising:
    an elongated catheter body portion;
    a first spiraled balloon about said elongated catheter body portion; and
    a second spiraled balloon about said elongated catheter body portion, wherein said first spiraled balloon is inflatable to a first size and said second spiraled balloon is inflatable to a second size when said first balloon is inflated to said first size, said first size different than said second size to enhance perfusion of a body fluid past said apparatus when inflated within a body lumen.

18. The catheter balloon arrangement of claim 17 wherein said first size and said second size are predetermined sizes.

19. The apparatus of claim 17 further comprising:
    a first inflation lumen coupled to said first spiraled balloon; and a second inflation lumen coupled to said second spiraled balloon.

20. A catheter balloon arrangement comprising:

a catheter body portion;

a first spiraled balloon coupled to said catheter body portion and having a first apex;

a second spiraled balloon coupled to said catheter body portion and having a second apex; and a pitch length between said first apex and said second apex, said pitch length to encourage tortuous compatibility between said catheter balloon arrangement and a tortuous body lumen when said catheter balloon arrangement is inflated within said tortuous body lumen, wherein said first spiraled balloon is inflatable to a first size and said second spiraled balloon is inflatable to a second size when said first balloon is inflated to said first size, said first size different than said second size to enhance perfusion of a body fluid past said catheter balloon arrangement when inflated within a body lumen.

21. The catheter balloon arrangement of claim 20 wherein said first size and said second size are predetermined sizes.

22. The catheter balloon arrangement of claim 20 further comprising:

a first inflation lumen coupled to said first spiraled balloon; and a second inflation lumen coupled to said second spiraled balloon.

23. A method comprising:

advancing a deflated catheter balloon arrangement through a body lumen to a treatment site, said catheter balloon arrangement including a first spiraled balloon and a second spiraled balloon about an elongated catheter body portion;

inflating said catheter balloon arrangement; and treating said body lumen at said treatment site, wherein said body lumen is a tortuous body lumen, said body lumen is a tortuous body lumen, said first spiraled balloon includes a first apex, said second spiraled balloon includes a inflation medium via a second inflation to achieve a second size, said first size different from said second size to enhance said perfusing.

24. The method of claim 23 further comprising perfusing a body fluid past said catheter balloon arrangement during said treating.

25. The method of claim 23 wherein said inflating further comprises:

filling said first spiraled balloon with a first inflation medium via a first inflation lumen to achieve a first size of said first spiraled balloon; and filling said second spiraled balloon with a second inflation medium via a second inflation to achieve a second size, said first size different from said second size to enhance said perfusing.

* * * * *